United States Patent
Beck, Jr. et al.

(10) Patent No.: US 9,907,646 B2
(45) Date of Patent: *Mar. 6, 2018

(54) FEMORAL FIXATION

(71) Applicant: DePuy Mitek, LLC, Raynham, MA (US)

(72) Inventors: Charles Beck, Jr., Holladay, UT (US); Jose E. Lizardi, Walpole, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/427,433

(22) Filed: Feb. 8, 2017

(65) Prior Publication Data

US 2017/0143473 A1 May 25, 2017

Related U.S. Application Data

(60) Continuation of application No. 14/996,384, filed on Jan. 15, 2016, now Pat. No. 9,592,115, which is a continuation of application No. 14/268,538, filed on May 2, 2014, now Pat. No. 9,265,602, which is a division of application No. 13/533,375, filed on Jun. 26, 2012, now Pat. No. 8,747,470, which is a
(Continued)

(51) Int. Cl.
  *A61F 2/08* (2006.01)
(52) U.S. Cl.
  CPC ..... *A61F 2/0811* (2013.01); *A61F 2002/0835* (2013.01); *A61F 2002/0852* (2013.01); *A61F 2002/0858* (2013.01); *A61F 2002/0882* (2013.01); *A61F 2210/0004* (2013.01)

(58) Field of Classification Search
  CPC ................. A61F 2/0811; A61F 2/0805; A61F 2002/0882; A61F 2002/0888
  USPC ..... 623/13.11–13.2; 606/263, 300–321, 326, 606/327; 411/42–44, 57.1–60.2, 63–66, 411/71–74
  See application file for complete search history.

(56) References Cited

U.S. PATENT DOCUMENTS

| RE13,204 E | 2/1911 | Jossabt |
| 2,353,851 A | 7/1944 | Rosan |
| 3,153,975 A | 10/1964 | Rapata |

(Continued)

FOREIGN PATENT DOCUMENTS

| CA | 1015989 A | 8/1977 |
| DE | 8914308 U1 | 3/1990 |

(Continued)

OTHER PUBLICATIONS

Extended European Search Report, from 11156055.3, dated May 3, 2011 (13 pages).

(Continued)

*Primary Examiner* — Matthew Lawson

(57) ABSTRACT

Various methods and devices are provided for a graft fixation device for fixing a graft member within a bone tunnel. In one embodiment, a graft fixation device is provided having a radially expandable sheath adapted to be disposed within a bone tunnel, and a sheath expander adapted to be received within the radially expandable sheath to expand the sheath and thereby anchor a graft between the sheath and the bone tunnel. In an exemplary embodiment, the graft fixation device is particularly useful to affix a graft within a femoral tunnel.

9 Claims, 8 Drawing Sheets

Related U.S. Application Data continuation of application No. 11/537,180, filed on Sep. 29, 2006, now Pat. No. 8,226,714.

(56) References Cited

U.S. PATENT DOCUMENTS

| | | |
|---|---|---|
| 3,199,398 A | 8/1965 | Weisz |
| 3,411,397 A | 11/1968 | Birmingham |
| 3,516,324 A | 6/1970 | Berner |
| 3,678,798 A | 7/1972 | Van Niel |
| 3,731,724 A | 5/1973 | Dorflinger |
| 3,765,295 A | 10/1973 | Ptak |
| 3,832,931 A | 9/1974 | Talan |
| 3,942,407 A | 3/1976 | Mortensen |
| 3,976,079 A | 8/1976 | Samuels et al. |
| 4,083,289 A | 4/1978 | Erickson |
| 4,085,651 A | 4/1978 | Koscik |
| 4,407,618 A | 10/1983 | Kimura |
| 4,484,570 A | 11/1984 | Sutter et al. |
| 4,535,925 A | 8/1985 | Ramey et al. |
| 4,580,936 A | 4/1986 | Francis et al. |
| 4,590,928 A | 5/1986 | Hunt et al. |
| 4,708,132 A | 11/1987 | Silvestrini |
| 4,708,397 A | 11/1987 | Weinmann |
| 4,716,893 A | 1/1988 | Fischer et al. |
| 4,744,793 A | 5/1988 | Parr et al. |
| 4,755,183 A | 7/1988 | Kenna |
| 4,778,468 A | 10/1988 | Hunt et al. |
| 4,784,126 A | 11/1988 | Hourahane |
| 4,828,562 A | 5/1989 | Kenna |
| 4,851,005 A | 7/1989 | Hunt et al. |
| 4,870,957 A | 10/1989 | Goble et al. |
| 4,927,421 A | 5/1990 | Goble et al. |
| 4,940,467 A | 7/1990 | Tronzo |
| 4,944,742 A | 7/1990 | Clemow et al. |
| 4,950,270 A | 8/1990 | Bowman et al. |
| 4,950,271 A | 8/1990 | Lewis et al. |
| 5,013,316 A | 5/1991 | Goble et al. |
| 5,037,422 A | 8/1991 | Hayhurst et al. |
| 5,062,843 A | 11/1991 | Mahony, III |
| 5,108,431 A | 4/1992 | Mansat et al. |
| 5,147,362 A | 9/1992 | Goble |
| 5,151,104 A | 9/1992 | Kenna |
| 5,152,790 A | 10/1992 | Rosenberg et al. |
| 5,211,647 A | 5/1993 | Schmieding |
| 5,234,430 A | 8/1993 | Huebner |
| 5,236,445 A | 8/1993 | Hayhurst et al. |
| 5,268,001 A | 12/1993 | Nicholson et al. |
| 5,282,802 A | 2/1994 | Mahony, III |
| 5,312,438 A | 5/1994 | Johnson |
| 5,314,427 A | 5/1994 | Goble et al. |
| 5,324,308 A | 6/1994 | Pierce |
| 5,356,435 A | 10/1994 | Thein |
| 5,360,448 A | 11/1994 | Thramann |
| 5,360,450 A | 11/1994 | Giannini |
| 5,376,119 A | 12/1994 | Zimmermann et al. |
| 5,383,878 A | 1/1995 | Roger et al. |
| 5,425,707 A | 6/1995 | Goldberg |
| 5,425,767 A | 6/1995 | Steininger et al. |
| 5,454,811 A | 10/1995 | Huebner |
| 5,458,601 A | 10/1995 | Young, Jr. et al. |
| 5,464,427 A | 11/1995 | Curtis et al. |
| 5,470,334 A | 11/1995 | Ross et al. |
| 5,480,403 A | 1/1996 | Lee et al. |
| 5,486,197 A | 1/1996 | Le et al. |
| 5,489,210 A | 2/1996 | Hanosh |
| 5,562,669 A | 10/1996 | McGuire |
| 5,584,835 A | 12/1996 | Greenfield |
| 5,618,314 A | 4/1997 | Harwin et al. |
| 5,632,748 A | 5/1997 | Beck, Jr. et al. |
| 5,645,589 A | 7/1997 | Li |
| 5,702,397 A | 12/1997 | Goble et al. |
| 5,707,395 A | 1/1998 | Li |
| 5,725,529 A | 3/1998 | Nicholson et al. |
| 5,776,196 A | 7/1998 | Matsuzaki et al. |
| 5,895,425 A | 4/1999 | Grafton et al. |
| 5,899,938 A | 5/1999 | Sklar et al. |
| 5,906,632 A | 5/1999 | Bolton |
| 5,918,604 A | 7/1999 | Whelan |
| 5,948,001 A | 9/1999 | Larsen |
| 5,961,520 A | 10/1999 | Beck, Jr. et al. |
| 5,989,253 A | 11/1999 | Bigliardi |
| 6,099,530 A | 8/2000 | Simonian et al. |
| 6,132,433 A | 10/2000 | Whelan |
| 6,283,973 B1 | 9/2001 | Hubbard et al. |
| 6,355,066 B1 | 3/2002 | Kim |
| 6,371,124 B1 | 4/2002 | Whelan |
| 6,379,361 B1 | 4/2002 | Beck, Jr. et al. |
| 6,387,129 B2 | 5/2002 | Rieser et al. |
| 6,517,579 B1 | 2/2003 | Paulos et al. |
| 6,533,816 B2 | 3/2003 | Sklar |
| 6,537,319 B2 | 3/2003 | Whelan |
| 6,554,862 B2 | 4/2003 | Hays et al. |
| 6,558,094 B2 | 5/2003 | Nehl |
| 6,562,071 B2 | 5/2003 | Jarvinen |
| 6,575,987 B2 | 6/2003 | Gellman et al. |
| 6,589,245 B1 | 7/2003 | Weiler et al. |
| 6,616,694 B1 | 9/2003 | Hart |
| 6,623,524 B2 | 9/2003 | Schmieding |
| 6,632,245 B2 | 10/2003 | Kim |
| 6,673,094 B1 | 1/2004 | McDevitt et al. |
| 6,733,529 B2 | 5/2004 | Whelan |
| 6,746,483 B1 | 6/2004 | Bojarski et al. |
| 6,887,271 B2 | 5/2005 | Justin et al. |
| 6,932,841 B2 | 8/2005 | Sklar et al. |
| 6,939,379 B2 | 9/2005 | Sklar |
| 7,008,451 B2 | 3/2006 | Justin et al. |
| 7,083,647 B1 | 8/2006 | Sklar et al. |
| 7,261,716 B2 | 8/2007 | Strobel et al. |
| 7,309,355 B2 | 12/2007 | Donnelly et al. |
| 7,329,281 B2 | 2/2008 | Hays et al. |
| 7,578,844 B2 | 8/2009 | Sklar et al. |
| 7,637,949 B2 | 12/2009 | Hart |
| 7,901,456 B2 | 3/2011 | Justin et al. |
| 8,048,158 B2 | 11/2011 | Hays et al. |
| 8,226,714 B2 | 7/2012 | Beck, Jr. et al. |
| 8,298,285 B2 | 10/2012 | Sklar et al. |
| 8,349,010 B2 | 1/2013 | Justin et al. |
| 8,470,037 B2 | 6/2013 | Re et al. |
| 8,562,680 B2 | 10/2013 | Hays et al. |
| 8,747,470 B2 | 6/2014 | Beck, Jr. et al. |
| 9,265,602 B2 | 2/2016 | Beck, Jr. et al. |
| 9,592,115 B2 | 3/2017 | Beck, Jr. et al. |
| 2001/0007074 A1 | 7/2001 | Strobel et al. |
| 2001/0047206 A1 | 11/2001 | Sklar et al. |
| 2002/0007182 A1* | 1/2002 | Kim .......................... 606/53 |
| 2002/0040241 A1 | 4/2002 | Jarvinen |
| 2002/0055780 A1 | 5/2002 | Sklar |
| 2002/0072797 A1 | 6/2002 | Hays et al. |
| 2003/0065390 A1* | 4/2003 | Justin ................ A61F 2/0811 |
| | | 623/13.14 |
| 2003/0135274 A1 | 7/2003 | Hays et al. |
| 2003/0144735 A1 | 7/2003 | Sklar et al. |
| 2003/0191530 A1 | 10/2003 | Sklar |
| 2004/0059415 A1 | 3/2004 | Schmieding |
| 2004/0068262 A1 | 4/2004 | Lemos et al. |
| 2004/0194789 A1 | 10/2004 | Whelan |
| 2004/0267361 A1* | 12/2004 | Donnelly ............ A61F 2/0811 |
| | | 623/13.14 |
| 2005/0159748 A1 | 7/2005 | Clark |
| 2005/0171603 A1 | 8/2005 | Justin et al. |
| 2005/0216012 A1 | 9/2005 | Willmen |
| 2006/0052787 A1 | 3/2006 | Re et al. |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0149258 A1 | 7/2006 | Sousa |
| 2006/0189991 A1 | 8/2006 | Bickley |
| 2007/0005069 A1 | 1/2007 | Contiliano et al. |
| 2007/0055255 A1 | 3/2007 | Siegel |
| 2008/0015710 A1 | 1/2008 | Hays et al. |
| 2008/0133007 A1 | 6/2008 | Donnelly et al. |
| 2008/0154314 A1 | 6/2008 | McDevitt |
| 2008/0161806 A1 | 7/2008 | Donnelly et al. |
| 2008/0161864 A1 | 7/2008 | Beck et al. |

(56) References Cited

U.S. PATENT DOCUMENTS

| | | |
|---|---|---|
| 2008/0228271 A1 | 9/2008 | Stone et al. |
| 2010/0121449 A1 | 5/2010 | Sklar et al. |
| 2010/0198258 A1 | 8/2010 | Heaven et al. |
| 2011/0112641 A1 | 5/2011 | Justin et al. |
| 2012/0053691 A1 | 3/2012 | Hays et al. |
| 2012/0265299 A1 | 10/2012 | Beck, Jr. et al. |
| 2014/0243978 A1 | 8/2014 | Beck, Jr. et al. |

FOREIGN PATENT DOCUMENTS

| | | | |
|---|---|---|---|
| DE | 9109381 | U1 | 9/1991 |
| DE | 4127550 | A1 | 2/1993 |
| EP | 72031 | A1 * | 2/1983 ............ F16B 13/124 |
| EP | 358372 | A1 | 3/1990 |
| EP | 425140 | A2 | 5/1991 |
| EP | 596177 | A1 | 5/1994 |
| EP | 596829 | A1 | 5/1994 |
| EP | 611557 | A2 | 8/1994 |
| EP | 651979 | A1 | 5/1995 |
| EP | 834281 | A1 | 4/1998 |
| EP | 1491162 | A2 | 12/2004 |
| FR | 2590792 | A1 | 6/1987 |
| FR | 2636835 | A1 | 3/1990 |
| FR | 2725615 | A1 | 4/1996 |
| JP | 2001-514545 | A | 9/2001 |
| JP | 05-300917 | B2 | 9/2013 |
| WO | WO-94/28799 | A1 | 12/1994 |
| WO | WO-98/22047 | A1 | 5/1998 |
| WO | WO-98/23229 | A1 | 6/1998 |
| WO | WO-99/52472 | A1 | 10/1999 |
| WO | WO-01/06909 | A2 | 2/2001 |
| WO | WO-01/30253 | A1 | 5/2001 |
| WO | WO-01/95835 | A1 | 12/2001 |
| WO | WO-02/32345 | A2 | 4/2002 |
| WO | WO-05/070314 | A1 | 8/2005 |

OTHER PUBLICATIONS

Office Action issued in Japanese Application No. 2007-254092 dated May 15, 2012. (8 pages).

Office action issued in Japanese Application No. 2013-122523 dated Feb. 2, 2016. (Japanese original and English translation).

Office action issued in Japanese Application No. 2013-122523 dated Jan. 6, 2015. (Japanese original and English translation).

Office action issued in Japanese Application No. 2015-078361 dated Feb. 16, 2016. (Japanese original and English translation).

Sklar, "Intrafix.TM. Technique for Tibial Fixation of ACL Grafts" Innovasive Devices, a company brochure of Mitek Products, Ethicon 1999—U.S. Appl. No. 09/304,885, Sklar et al., filed May 4, 1999.

\* cited by examiner

FEMORAL FIXATION

CROSS REFERENCE TO RELATED APPLICATIONS

The present application is a continuation of U.S. patent application Ser. No. 14/996,384, filed Jan. 15, 2016, and entitled "FEMORAL FIXATION," which is a continuation of U.S. patent application Ser. No. 14/268,538 (now U.S. Pat. No. 9,265,602), filed May 2, 2014, and entitled "FEMORAL FIXATION," which is a divisional of U.S. patent application Ser. No. 13/533,375 (now U.S. Pat. No. 8,747,470), filed Jun. 26, 2012, and entitled "FEMORAL FIXATION," which is a continuation of U.S. patent application Ser. No. 11/537,180 (now U.S. Pat. No. 8,226,714), filed Sep. 29, 2006, and entitled "FEMORAL FIXATION," each of which are hereby incorporated by reference in their entireties.

BACKGROUND

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents or overexertion. Accordingly, various procedures have been developed to repair or replace such damaged ligaments. For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the ACL is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

A number of devices are currently employed for anchoring graft ligaments in the femur, including the use of crosspins, interference screws, and buttons which seat against the cortex of the femur when tension is applied to the graft ligament. A number of problems result from these techniques. For example, the button is placed deep within the femoral tunnel and away from the joint line, which can cause the graft to move in a side-to-side motion, i.e., to have a windshield wiper effect, and to cause tunnel widening, potentially leading to joint laxity. Other common problems involved in femoral fixation include slippage of the device within the femoral tunnel, slippage of the graft ligament relative to the device, or damage to the graft ligament resulting from contact with the device itself, such as the graft ligament being lacerated or wound up causing the graft orientation to be altered by the device.

Accordingly, there remains a need for a graft ligament anchor which is simple, easy to install, and inexpensive to manufacture, while providing secure, trouble-free anchoring of the graft ligament.

SUMMARY

The present invention generally provides a methods and devices for fixing a graft member within a bone tunnel. In one embodiment, a graft fixation device is provided which includes a radially expandable sheath having proximal and distal ends with three sidewalls extending therebetween and defining a central lumen. The sheath can have a substantially triangular cross-sectional shape. The graft fixation device also includes a sheath expander, for example, a tapered screw, adapted to be disposed in the central lumen of the radially expandable sheath and configured to flex the three sidewalls to radially expand the sheath so as to fix a graft member extending between the sheath and a bone tunnel within the bone tunnel.

In one exemplary embodiment, the three sidewalls can be at least partially separated by three longitudinally oriented slots extending therebetween. For example, each sidewall can be connected by a proximal attachment point and a distal attachment point, with the slots extending between the proximal and distal attachment points. In another embodiment, two of the sidewalls, e.g., the first and second sidewalls, can have a substantially concave outer surface adapted to seat a graft member, and a third sidewall can have a substantially convex outer surface adapted to engage a bone tunnel. The sidewalls can also include radially oriented ridges formed thereon.

The radially expandable sheath and sheath expander can also include other features. For example, a proximal-most end of the radially expandable sheath can be angled relative to a longitudinal axis of the radially expandable sheath. In another embodiment, the sheath expander and a distal-most end of the radially expandable sheath each can include a lumen extending therethrough for receiving a guide wire. In other embodiments, the radially expandable sheath can include a stop member formed on a proximal end thereof and adapted to prevent over-insertion of the radially expandable sheath into a bone tunnel. The dimensions of and materials used to form the expandable sheath and sheath expander can also vary. Preferably, the sheath expander has a maximum outer diameter that is greater than a maximum inner diameter of the radially expandable sheath in an unexpanded state, and the sheath expander and the radially expandable sheath are formed from a biocompatible and/or bioabsorbable material. In another embodiment, the distal end of the expandable sheath can include a cradle for seating the graft therein.

In another embodiment of the invention, a graft fixation device is provided that includes an elongate expandable sheath having three sidewalls extending between proximal and distal ends. The three sidewalls can be attached to one another at a proximal attachment point and a distal attachment point, and they can be separated from one another by three longitudinal slots extending between the proximal and distal attachment points. The graft fixation device also includes an expander disposable within the expandable sheath and adapted to expand the sheath such that the proximal attachment points break to separate the sidewalls at the proximal end of the sheath.

Exemplary methods for fixing a ligament graft in a bone tunnel are also provided, and in one embodiment the method can include positioning a leading end of a graft within a femoral tunnel such that a trailing end of the grafts extends through a tibial tunnel. A flexible sheath can be inserted into the femoral tunnel, and it can have a substantially triangular cross-sectional shape such that flexible sheath positions the graft on a posterior side of the femoral tunnel. The method can further include inserting an expansion plug into the flexible sheath to expand the flexible sheath and thereby fix the leading end of the graft within the femoral tunnel. The method can also include inserting a graft fixation device into the tibial tunnel to fix the trailing end of the graft within the tibial tunnel. The graft can include two or more bundles or strands, with each strand being looped at the leading end of the graft around a distal end of the flexible sheath. The flexible sheath can include a cradle disposed on a distal end thereof for securing the strands at the leading end of the graft. In one exemplary embodiment, positioning the leading end of the graft can include looping the leading end of the graft around a length of suture, and pulling the suture through the tibial and femoral tunnels to pull the leading end of the graft into the femoral tunnel.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for fixing a graft member in a bone tunnel. In general, a graft fixation device is provided having an expandable sheath with a central lumen formed therethrough, and a sheath expander that is adapted to expand the expandable sheath to fix a graft member within a bone tunnel. While the device can be used to fix a graft member within any bone, in an exemplary embodiment the device is adapted for use in the femoral tunnel. The device can thus include certain features to facilitate positioning of the graft at a location that will reduce the risk of damage to the graft, as well as other features to facilitate femoral fixation. In one exemplary embodiment, the device is configured to facilitate positioning of individual anteromedial and posterolateral bundles of a graft at a location which corresponds to the position of anteromedial and posterolateral bundles of a natural ligament. A person skilled in the art will appreciate that the term "graft member" as used herein is intended to encompass a variety of materials, such as natural ligaments and tendons, synthetic grafts and tendons, sutures, or any other material that needs to be anchored within a bone tunnel. The various components of the device can also be formed from a variety of materials, but in an exemplary embodiment the expandable sheath and sheath expander are formed from a biocompatible material. The components can also be formed from a bioabsorbable, biocompatible material, such as polylactic acid (PLA). However, it is understood that other suitable biocompatible and optionally bioabsorbable polymers can also be used.

FIGS. 1-5 illustrate one exemplary embodiment of a graft fixation device. As shown, the graft fixation device 10 generally includes a radially expandable sheath 12 for attaching a ligament graft to bone, and a sheath expander 14 that is adapted to be disposed in a central lumen of the radially expandable sheath 12 and that is configured to radially expand the sheath 12 so as to fix a graft member within a bone tunnel.

Figure 1:
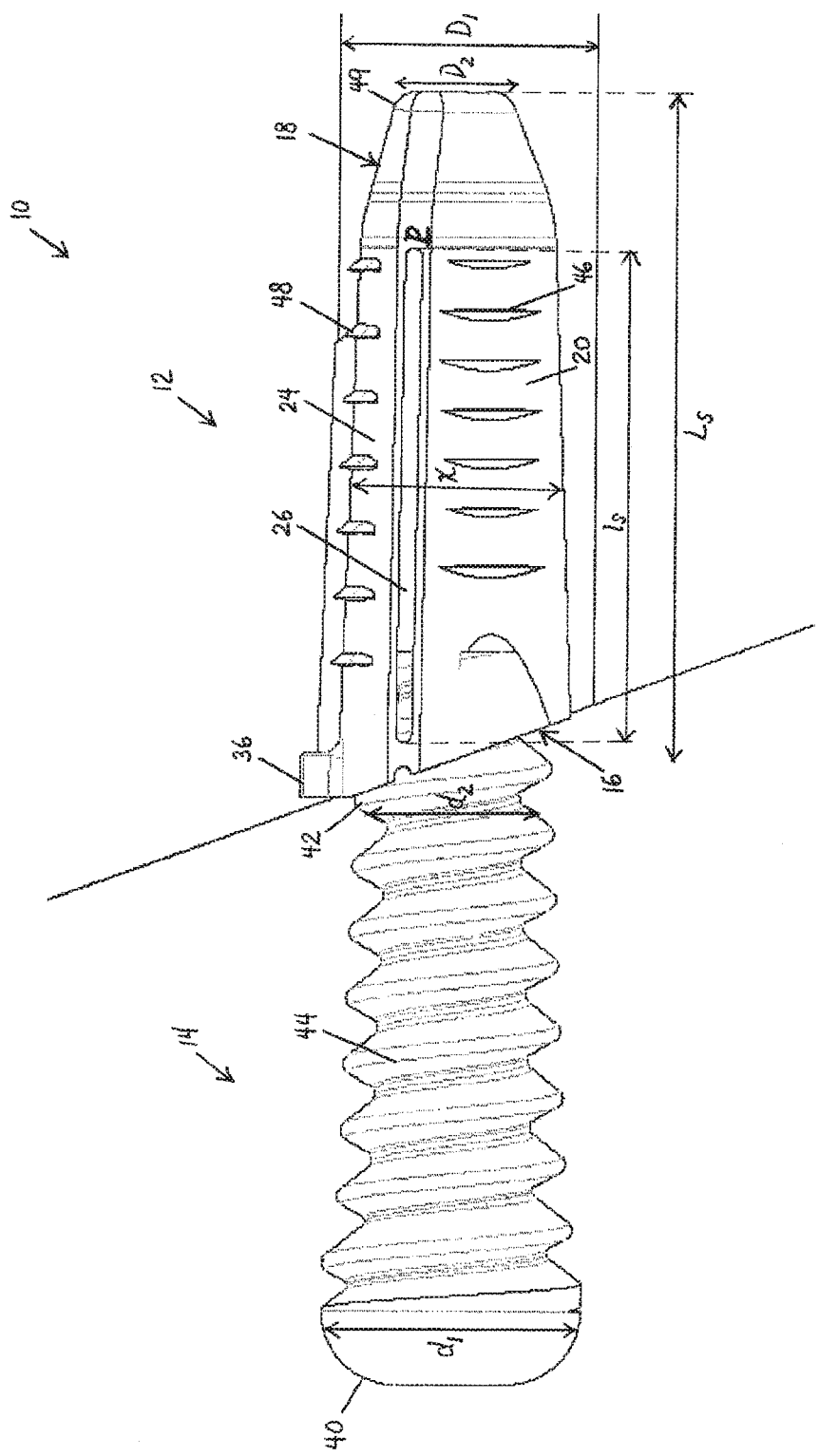
FIG. 1 is a side view of a radially expandable sheath and a sheath expander in accordance with one embodiment of the invention.
Figure 2:
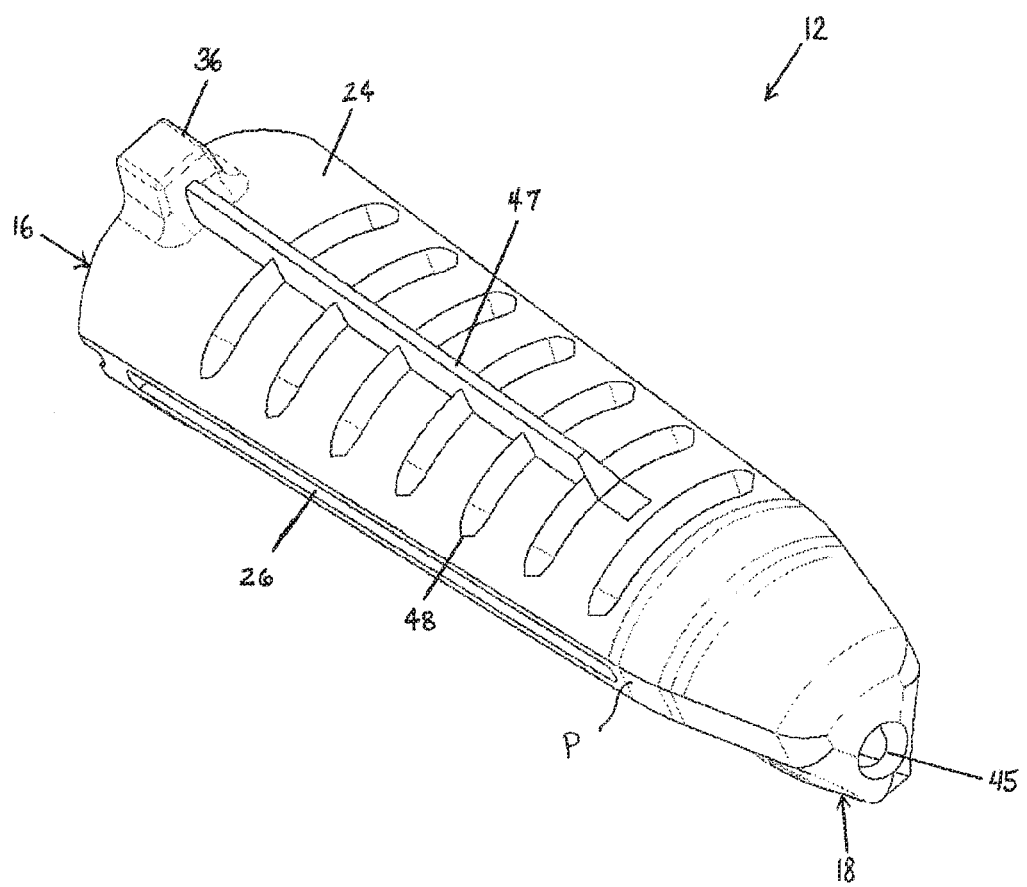
FIG. 2 is a perspective view of the radially expandable sheath shown in FIG. 1
Figure 3:
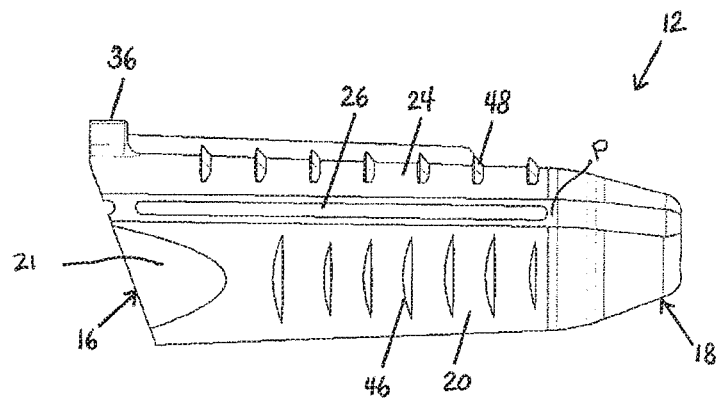
FIG. 3 is a side view of the radially expandable sheath shown in FIG. 1.
Figure 4:
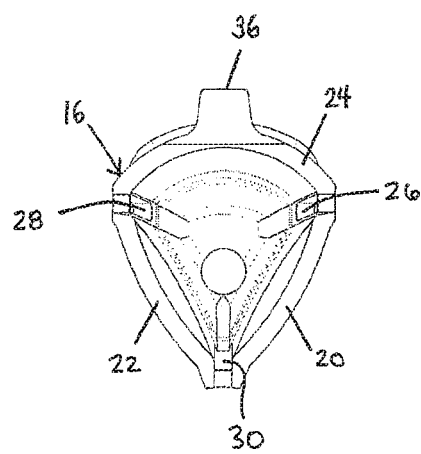
FIG. 4 is an end view of a distal end of the radially expandable sheath shown in FIG. 1.

The expandable sheath 12 can have any shape and size but it should be adapted to expand within a bone tunnel to attach a graft to bone. In the illustrated embodiment, shown in more detail in FIGS. 2-4, the expandable sheath 12 has an elongate configuration with an inner lumen extending between a trailing proximal end 16 and a leading distal end 18 thereof. While the cross-sectional shape of the sheath 12 can vary, in an exemplary embodiment, the sheath 12 has a substantially triangular cross-sectional shape defined by three sidewalls 20, 22, 24 extending between the proximal and distal ends 16, 18 of the sheath 12. Each sidewall 20, 22, 24 can taper from a proximal end 16 of the sheath 12 to a distal end 18 of the sheath 12 to form a sheath 12 having a bullet-shaped profile. As a result, the proximal end 16 of the sheath 12 defines the largest outer diameter $D_1$ of the sheath 12, and the distal end 18 defines the smallest outer diameter $D_2$ of the sheath 12, as shown in FIG. 1. The sheath 12 also includes an inner diameter x which is the largest at its proximal end 16 and decreases towards its distal end 18. The proximal end 16 of the sheath 12 can optionally be angled, as shown in FIGS. 1 and 3, to match an opening of a bone tunnel. The proximal end 16 of the sheath 12 can also optionally be flared and/or can include a lead-in to facilitate insertion of a threaded expander screw therein. For example, an inner surface of a proximal end of one or more of the sidewalls 20, 22, 24 can include a conical taper formed thereon to facilitate engagement of the expander screw 14 with one or more threads formed in the sheath 12, as will be discussed in more detail below. FIG. 3 illustrates a conical taper 21 formed in the proximal end of sidewall 20.

Each sidewall 20, 22, 24 of the sheath 12 is preferably separated from an adjacent sidewall by a longitudinally oriented slot 26, 28, 30 extending therebetween. Each slot 26, 28, 30 can have the same length ls, or alternatively the length of each slot 26, 28, 30 can vary with respect to one another. In an exemplary embodiment, each slot 26, 28, 30 has the same length ls and originates at or adjacent to the proximal end 16 of the sheath 12 and extends along a substantial length Ls of the sheath to allow the sidewalls to flex with respect to each other. Each slot 26, 28, 30 preferably terminates at the same position P just proximal to the distal end 18 of the sheath 12 to provide a slot-free distal tip. This termination point P defines the area at which each sidewall 20, 22, 24 will bend during expansion of the sheath 12 by a sheath expander 14. Thus, while the termination point P can vary, the distance between the termination point P at the end of each slot 26, 28, 30 and the distal end 18 of the sheath 12 should be sufficient to provide structural integrity to the device such that the sidewalls 20, 22, 24 do not break apart from one another or from the distal tip during expansion. The sidewalls 20, 22, 24 can also optionally be connected to one another at or adjacent to the proximal end 16 of the sheath 12. In one exemplary embodiment, the connections between the sidewalls 20, 22, 24 can split or break when the sheath expander 14 is inserted into the central lumen of the sheath 12.

Each sidewall 20, 22, 24 of the sheath 12 can also have a variety of shapes and sizes. In an exemplary embodiment, each of the first and second sidewalls 20, 22 has a substantially concave outer surface that is adapted to seat a graft, and the third sidewall 24 has a substantially convex outer surface that is adapted to engage a bone tunnel. The concave surface of the first and second sidewalls 20, 22, and the convex surface of the third sidewall 24 preferably extend along the length ls of the sidewalls 20, 22, 24. The proximal-most portion of each sidewall 20, 22, 24, however, can include a flared region to provide an enlarged opening to the central lumen to facilitate insertion of the sheath expander 14 therein. The first and second sidewalls 20, 22 can also include one or more surface features formed thereon to facilitate engagement of a graft 100 between the sidewalls 20, 22 and the bone tunnel when the sheath is implanted, and the third sidewall 24 can include one or more surface features formed thereon to facilitate engagement with the bone tunnel. The surface features can have a variety of configurations, and can be formed on all or a portion of one or more of the sidewalls 20, 22, 24. As shown in FIGS. 1-3, the surface features are formed from a series of transversely-oriented ridges 46, 48 formed along a substantial portion of each sidewall 20, 22, 24. In other words, the ridges 46, 48 extend radially around the sheath 12. The ridges 46 formed on the first and second sidewalls 20, 22 can be effective to engage or grip the graft 100 to prevent sliding movement of the graft 100 with respect to the sheath 12, and the ridges 48 formed on the third sidewall 24 can be effective to engage the bone tunnel to prevent movement of the device 10 within the bone tunnel. In an exemplary embodiment, the ridges 46 formed on the first and second sidewalls 20, 22 are positioned in an opposite direction to the ridges 48 formed on the third sidewall 24. In particular, the ridges 46 formed on the first and second sidewalls 20, 22 can be angled and pointed toward the distal end 18 of the sheath 12 to prevent a graft from sliding proximally, and the ridges 48 formed on the third sidewall 24 can be angled and pointed toward the proximal end 16 of the sheath 12 to prevent the sheath 12 from sliding proximally. A person skilled in the art will appreciate that the sheath 12 can include a variety of different features to facilitate engagement between the sheath 12 and the graft and the sheath 12 and the bone tunnel. For example, as further shown in FIG. 2, the sheath can include an axial rib 47 extending between the proximal and distal ends 16, 18 of the sheath 12. The axial rib 47 can help prevent rotation of the sheath 12 within the bone tunnel.

One or more sidewalls can also optionally include a stop member adapted to prevent over-insertion of the sheath 12 into a bone tunnel. While the stop member can have a variety of configurations, FIGS. 1-2 illustrate one exemplary embodiment of a stop member 36 formed on the proximal-most end of the sheath 12, and in particular on one of the sidewalls, e.g., sidewall 24. The stop member 36 can have a variety of configurations, but in the illustrated embodiment, the stop member 36 is in the form of a tab-like protrusion that extends radially outward from the proximal end 16 of the sheath 12. As a result, the stop member 36 will abut the edge of a bone tunnel during insertion of the sheath 12 into the bone tunnel, thereby preventing over-insertion of the sheath 12.

The distal tip 49 of the sheath 12 can also have a variety of configurations, shapes and sizes. Since the distal tip 49 connects the three sidewalls 20, 22, 24 to one another to provide structural integrity to the sheath 12, the distal tip 49 is preferably slot-free, and also preferably does not include any surface features formed thereon. While the shape of the distal tip 49 can vary, the distal tip preferably originates adjacent to the termination point P of each longitudinal slot, and tapers toward the distal-most end of the sheath 12. The distal tip 49 can optionally include a flattened distal-most surface (shown in FIG. 1) for seating a graft therearound. The edges (not shown) that connect to the flattened surface are preferably rounded to form a substantially conical distal tip 49. The distal tip 49 can also optionally include a bore 45 (shown in FIG. 2) extending through the flattened surface for receiving a guide wire therethrough to facilitate implantation of the device 10. A person skilled in the art will appreciate that the distal tip 49 of the sheath 12 can have virtually any shape and size, and can optionally be substantially open or closed.

Figure 5:
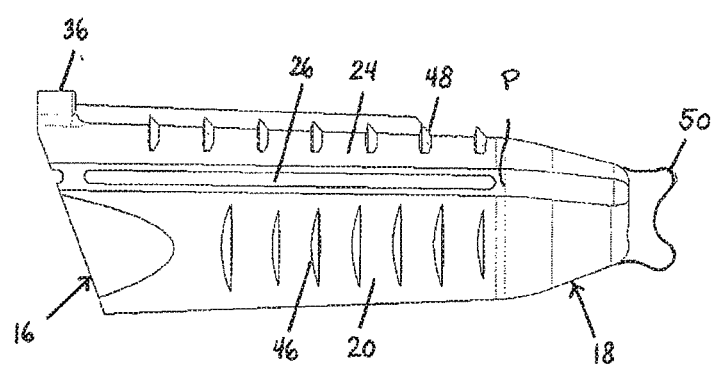
FIG. 5 is a side view of a radially expandable sheath in accordance with another exemplary embodiment of the invention having a feature disposed on the distal end of the sheath for seating a graft to prevent the graft from slipping.

In another embodiment, the distal tip 49 can include features to seat a graft to prevent the graft from slipping. For example, the distal tip 49 can include a cradle 50 disposed on the distal end 18, as shown in FIG. 5. The cradle 50 can include opposed longitudinally-oriented fingers formed on the distal end of the distal tip 49 and adapted to seat the graft therebetween. Each of the two bundles which make up the graft can be looped around one of the fingers to prevent the graft from slipping. A person skilled in the art will appreciate that the cradle 50 can have a variety of configurations for securing the graft at the distal tip of the expandable sheath 12, and that the distal tip 49 can have various other configurations to seat a graft to prevent the graft from slipping.

Referring back to FIG. 1, a sheath expander 14 can be used to expand the expandable sheath 12 once the sheath 12 is inserted into a bone tunnel. While the sheath expander 14 can have virtually any configuration, FIG. 1 illustrates one exemplary embodiment of a sheath expander 14 in the form of a tapered screw. The screw 14 includes a proximal end 40 defining the largest diameter $d_1$ of the screw, and a distal end 42 defining the smallest diameter $d_2$ of the screw. Threads 44 are formed around the screw and extend from the proximal end 40 to the distal end 42. In use, the screw 14 is adapted to expand the expandable sheath 12, thus the largest diameter $d_2$ of the screw 14 is preferably larger than the largest inner diameter x (FIG. 1) of the sheath 12, and more preferably it is at least as large as the largest outer diameter $D_1$ of the sheath 12. The screw 14 is disposed in the central lumen of the expandable sheath 12 and is configured to flex the three sidewalls 20, 22, 24 and break the connections between the sidewalls 20, 22, 24 at the proximal end 16 of the sheath 12 to radially expand the sheath 12 to fix the graft within a bone tunnel. The expander screw 14 can also include a socket formed in the proximal end thereof for receiving a driver tool, such as a hex wrench, that is effective to drive the screw 14 into the sheath 12. The expander screw 14 can also include a lumen (not shown) extending therethrough for receiving a guide wire to facilitate insertion of the screw 14 into the sheath 12. As previously stated, a person skilled in the art will appreciate the sheath expander 14 can have a variety of configurations, shapes, and sizes. A person skilled in the art will appreciate that a variety of implants having virtually any configuration can be used to expand the expandable sheath, and that sheath expander is merely one embodiment of an implant that can be used with the expandable sheath.

Figure 6:
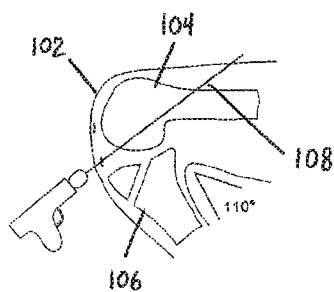
FIG. 6 is a side view of a knee being prepared for the insertion of a radially expandable sheath and sheath expander, showing a guide pin inserted through the knee.
Figure 7:
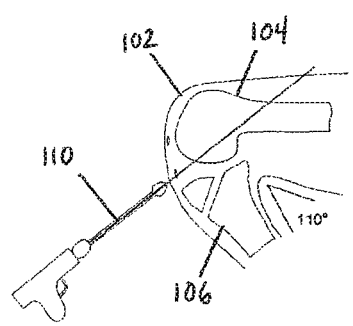
FIG. 7 is a side view of the knee of FIG. 6, showing a reamer inserted over the guide pin.
Figure 8:
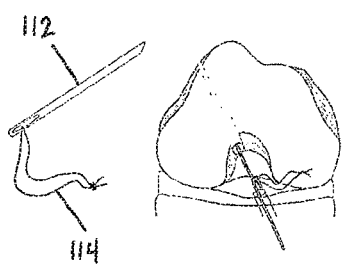
FIG. 8 is a top view of the knee of FIG. 7, showing a passing pin about to be inserted into a socket formed in the femur.
Figure 9:
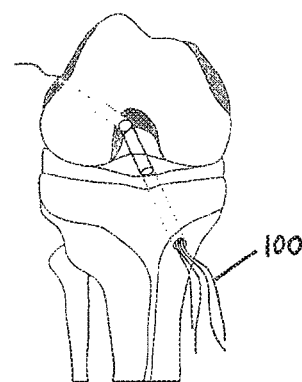
FIG. 9 is a front view of the knee of FIG. 8, showing a graft inserted through femoral and tibial tunnels.

The expandable sheath and sheath expander can be used in a variety of medical procedures, but they are preferably used to anchor ligaments within a bone tunnel. In an exemplary embodiment, the device is used for femoral fixation of a ligament graft. FIGS. 6-12 illustrate one exemplary method of ligament graft fixation. A person skilled in the art will appreciate that various other techniques known in the art can be used to perform each of the various steps of the procedure. In general, a graft can be prepared from two graft strands that are folded over to created a right bundle and a left bundle (or an anteromedial bundle and a posterolateral bundle), with each bundle having a portion of both graft strands. A length of suture can be whip stitched to each graft portion. As shown in FIG. 6, the knee 102 is flexed and a guide pin 108 is placed in the knee 102 and through the femoral cortex. In one embodiment, the knee 102 is flexed to 110 degrees and the guide pin 108 is drilled through the femur 104. A reamer 110 can be inserted over the guide pin 108, as shown in FIG. 7, in order to drill a tunnel or socket in the femur 104, after which the guide pin 108 and reamer 110 are removed. As shown in FIG. 8, a passing pin 112 holding a loop of suture 114 is placed through the socket formed in the femur 104. The other end of the suture loop 114 is then pulled through the tunnel formed in the tibia 106 using a hook (not shown). A graft 100 is then passed through the tunnel in the femur 104 by passing the sutures attached to the graft 100 through the suture loop 114 and pulling the suture loop 114 and the passing pin 112 through the femoral tunnel, as shown in FIG. 9.

Figure 10:
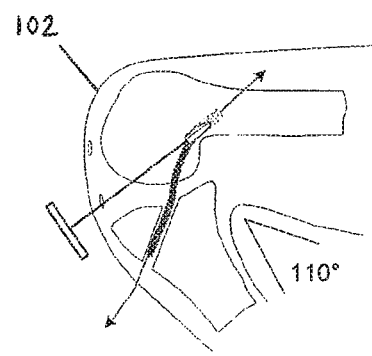
FIG. 10 is a side view of the knee of FIG. 9, showing a radially expandable sheath being advanced into the socket formed in the femur.

While tensioning the graft 100, the expandable sheath 12 can be inserted into the opening of the bone tunnel in femur 104, as shown in FIG. 10, preferably by sliding the sheath 12 along a guide wire extending through the tunnel. A mallet or other impacting device can be used to gently advance the sheath 12 into the tunnel. The stop member, if provided, will abut the opening of the tunnel when the sheath 12 is fully inserted. In this position, the graft bundle is preferably seated within the two sidewalls of the expandable sheath 12 that have concave outer surfaces, e.g., sidewalls 20, 22. A tool, such as a spatula, can optionally be used to separate the graft bundles and position them as desired relative to the sheath 12. The angled distal end of the sheath 12 can also be aligned with the opening of the tunnel, such that no portion of the sheath 12, other the stop member, remains external to the tunnel.

Figure 11:
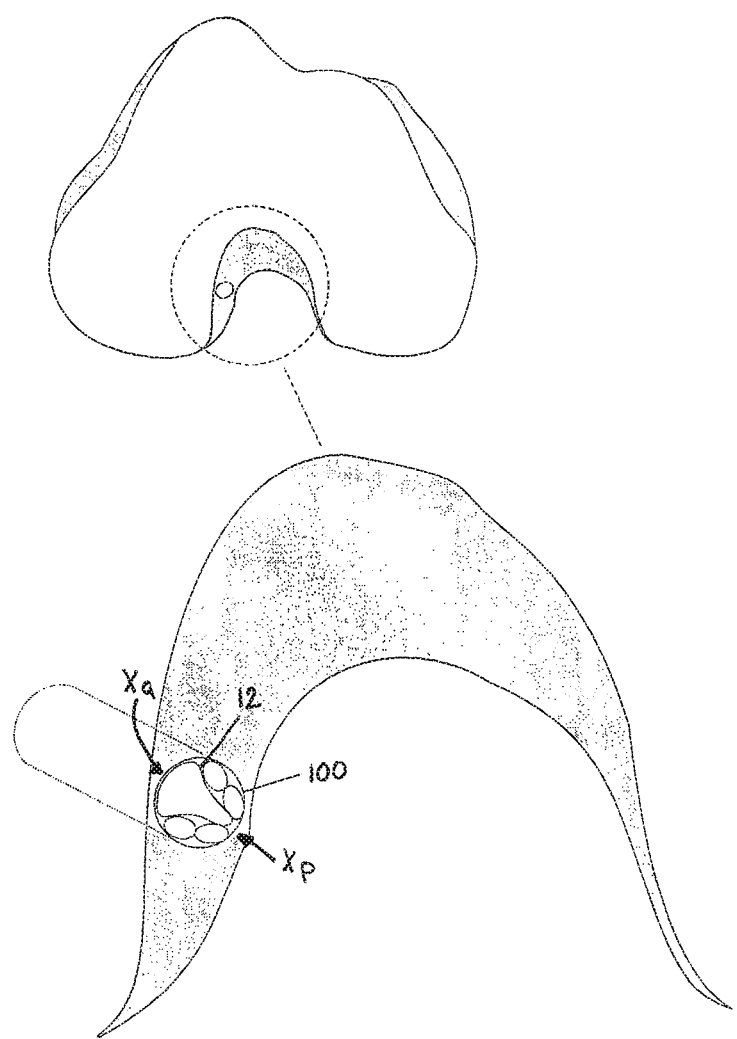
FIG. 11 is a cross-sectional view of the femur of the knee of FIG. 10, showing the radially expandable sheath with a sheath expander disposed therein.
Figure 12:
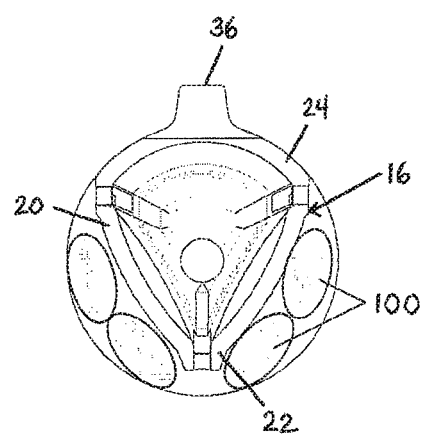
FIG. 12 is an end view of the proximal end of the radially expandable sheath disposed within the femoral tunnel of the knee of FIG. 11.

The sheath expander 14, e.g., tapered expander screw, can then be slowly inserted into the central lumen of the sheath 12, for example, using a driver tool, to expand the sidewalls 20, 22, 24 of the sheath 12. The conical taper formed in the proximal end of each sidewall 20, 22, 24 of the sheath 12 can facilitate alignment and engagement of the threads on the sheath expander 14 with the threads formed in the sheath 12. As the sheath expander 14 is driven into the sheath 12, the sidewalls 20, 22, 24 of the sheath 12 will deform outward toward a circular geometry to conform with an outer diameter of the expander 14. As a result, the concave sidewalls 20, 22 will compress the graft bundles against the bone tunnel wall, as shown in FIGS. 11-12. The ridges 48 formed on the sidewalls 20, 22 will engage the graft to prevent the graft from being pulled out of the tunnel. The third sidewall 24 will be compressed against the bone tunnel wall to engage the wall. The ridges 48 formed on the third sidewall 24 will help prevent the sheath 12 from being pulled out of the bone tunnel. Once the graft 100, the sheath 12, and the sheath expander 14 are positioned within the bone tunnel, the placement of the graft 100, as shown in FIG. 12, will secure the graft 100 within the femoral tunnel. The triangular orientation of the sheath 12 is also advantageous in that it can be used to position the graft towards the posterior side of the tunnel, creating a fan-like orientation with the graft strands. In this configuration, the graft strands mimics the position of a natural graft. In particular, the triangular orientation of the sheath 12 causes the graft strands to be positioned at a location in which a natural graft would normally be positioned, thus the graft strands will mimic the function of a natural graft. During bending of the knee, the graft will extend over the anterior side Xa (FIG. 11) of the tunnel, and thus over the head of the sheath expander. Since the sheath 12 compresses the graft toward the posterior side Xp (FIG. 11) of the tunnel, the graft is prevented from rubbing against the anterior edge Xa of the bone tunnel, thereby reducing the risk of damage to the graft. As noted above, this orientation also more closely mimics the anatomic footprint of the native ACL, adding rotational stability to the joint.

In another embodiment, a kit may be provided to a surgeon that includes a variety of expandable sheaths and sheath expanders to accommodate a variety of procedures and graft sizes. For example, multiple sheaths with a variety of sizes, including sheaths of different lengths and diameters, may be provided to be used with a variety of bone tunnels of different sizes. Multiple sheath expanders having different sizes may also be provided in the kit for use with a single size sheath to accommodate different sized grafts.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A method for fixing a ligament graft in a bone tunnel, comprising:
 positioning a leading end of a graft within a bone tunnel, the graft having a trailing end that extends through a tibial tunnel;

inserting a flexible sheath into the bone tunnel, the flexible sheath having first, second, and third sidewalls that define an inner lumen extending through the flexible sheath, the flexible sheath having a substantially triangular cross-sectional shape perpendicular to a longitudinal axis of the flexible sheath such that flexible sheath positions the graft on a posterior side of the bone tunnel, the flexible sheath having a stop member formed on a proximal-most end of the first sidewall with a distal face of the stop member being distal to a proximal-most surface of the second and third sidewalls, and the stop member abutting an edge of the bone tunnel during insertion to prevent over-insertion of the flexible sheath, and the proximal-most end of the flexible sheath being angled to align with the edge of the bone tunnel; and inserting a screw into the flexible sheath to expand the flexible sheath and thereby fix the leading end of the graft within the bone tunnel.

2. The method of claim 1, wherein inserting the screw into the flexible sheath includes engagement of the screw with one or more threads formed on an inner surface of the flexible sheath.

3. The method of claim 1, wherein inserting the screw into the flexible sheath includes inserting the screw into the inner lumen.

4. The method of claim 1, wherein expansion of the flexible sheath includes deformation of the first, second, and third sidewalls such that the substantially triangular cross-sectional shape of the flexible sheath changes to a different shape.

5. The method of claim 4, wherein the different shape conforms to a shape of an outer diameter of the screw.

6. The method of claim 1, wherein the first, second, and third sidewalls are each connected by a proximal attachment point and a distal attachment point.

7. The method of claim 1, wherein expansion of the flexible sheath includes a substantially convex outer surface of the first sidewall engaging the bone tunnel.

8. The method of claim 1, wherein expansion of the flexible sheath includes surface features formed on the second and third sidewalls engaging the graft, and surface features formed on the first sidewall engaging bone within the bone tunnel.

9. The method of claim 1, further comprising inserting a guide wire through the inner lumen of the flexible sheath.

* * * * *